(12) United States Patent
Hoegl et al.

(10) Patent No.: US 8,409,638 B2
(45) Date of Patent: Apr. 2, 2013

(54) SOLID HOMOGENEOUS MIXTURE OF POLYVINYLACETATE AND VINYLACETATE-VINYL LAURATE COPOLYMER PREPARED BY SEQUENTIAL SOLUTION POLYMERIZATION

(75) Inventors: Christian Hoegl, Reut (DE); Daniel Maedge, Burghausen (DE); Thomas Wimmer, Burghausen (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 13/480,592

(22) Filed: May 25, 2012

(65) Prior Publication Data

US 2012/0231113 A1    Sep. 13, 2012

Related U.S. Application Data

(60) Continuation of application No. 13/204,923, filed on Aug. 8, 2011, now abandoned, which is a division of application No. 12/057,437, filed on Mar. 28, 2008, now Pat. No. 8,017, 707.

(60) Provisional application No. 60/909,497, filed on Apr. 2, 2007.

(51) Int. Cl.
*A23G 4/06* (2006.01)
(52) U.S. Cl. .................. 426/6; 426/3; 524/524; 525/55; 525/222
(58) Field of Classification Search .................. 426/3, 6; 524/524; 525/55, 222
See application file for complete search history.

(56) References Cited

U.S. PATENT DOCUMENTS

| | | | |
|---|---|---|---|
| 3,519,587 | A | 7/1970 | Wiest et al. |
| 4,968,511 | A | 11/1990 | D'Amelia et al. |
| 5,173,317 | A | 12/1992 | Hartman et al. |
| 5,492,791 | A | 2/1996 | Marez |
| 5,601,858 | A | 2/1997 | Mansukhani et al. |
| 6,200,608 | B1 | 3/2001 | Gmunder et al. |
| 2003/0195319 | A1 | 10/2003 | Tschirner et al. |
| 2004/0052899 | A1 | 3/2004 | Corriveau et al. |
| 2007/0042079 | A1 | 2/2007 | Miladinov |
| 2007/0231424 | A1 | 10/2007 | Castro et al. |

FOREIGN PATENT DOCUMENTS

| | | |
|---|---|---|
| EP | 0 014 420 A2 | 8/1980 |
| EP | 0603642 A1 | 6/1994 |
| EP | 0 763 328 A1 | 3/1997 |
| EP | 1 352 914 B1 | 6/2006 |
| GB | 2 143 416 A | 2/1985 |
| WO | 2007/024903 A1 | 3/2007 |

OTHER PUBLICATIONS

XP002486166 of Apr. 4, 2007 from IP.com.

*Primary Examiner* — David W Wu
*Assistant Examiner* — Marie Reddick
(74) *Attorney, Agent, or Firm* — Brooks Kushman P.C.

(57) ABSTRACT

The invention provides a chewing gum base containing a homogeneous composition in solid form comprising
a) from 50 to 90% by weight of polyvinyl acetate and
b) from 10 to 50% by weight of vinyl acetate-vinyl laurate copolymer, the weight percentage based on the total weight of the composition.

11 Claims, No Drawings

US 8,409,638 B2

SOLID HOMOGENEOUS MIXTURE OF POLYVINYLACETATE AND VINYLACETATE-VINYL LAURATE COPOLYMER PREPARED BY SEQUENTIAL SOLUTION POLYMERIZATION

CROSS-REFERENCE TO RELATED APPLICATION

This application is a continuation of U.S. application Ser. No. 13/204,923, filed Aug. 8, 2011, which is a division of U.S. application Ser. No. 12/057,437, filed Mar. 28, 2008, now U.S. Pat. No. 8,017,707, issued Sep. 13, 2011, which, in turn, claims the benefit of U.S. provisional Application No. 60/909,497, filed Apr. 2, 2007 (now abandoned). The disclosure(s) of which are incorporated in their entirety by reference herein.

BACKGROUND OF THE INVENTION

1. Field of the Invention

The invention relates to compositions composed of polyvinyl acetate and vinyl acetate-vinyl laurate copolymer, to processes for their production and to their use in chewing gum base.

2. Background Art

Typically, chewing gum formulations are composed of a water-insoluble chewing gum base and a water-soluble fraction, the latter comprising sweeteners and flavorings which are leached out by the saliva during chewing.

In general, in the production of chewing gum base, in addition to solid elastomers, for example polyisobutylene, isobutylene/isoprene copolymers and/or butadiene/styrene copolymers, a vinyl acetate homopolymer is used as a polymer resin. Suitable elastomer solvents are, for example, polyterpenes or glyceryl esters of rosin or partially hydrogenated rosin. The plasticizers used are frequently hydrogenated vegetable oils, cocoa butter, paraffin waxes, natural waxes and polyethylene. Additional plasticization is achieved by the use of triacetin, and/or emulsifiers such as glyceryl monostearate, acetylated monoglycerides of natural fatty acids and/or lecithin.

The chewing gum bases can be produced in one or more stages. Typically, in a batchwise process, mixers or double-Z kneaders with high shear force are used for this purpose. Alternatively, EP 0763328 describes continuous processes in which the chewing gum base is produced in an extruder.

U.S. Pat. No. 4,968,511 recommends using, as the chewing gum base, one or more polymers such as homopolymers of vinyl esters of carboxylic acids having from 3 to 10 carbon atoms, copolymers of two different vinyl esters, copolymers of vinyl ester and ethylene, and the terpolymers of vinyl alcohol, vinyl ester and ethylene. To produce the gum base, the individual constituents of the formulation, such as polymer resin, elastomer, filler and emulsifier, are metered successively into a preheated mixer.

U.S. Pat. No. 5,173,317 discloses the use of vinyl acetate-vinyl laurate copolymers instead of polyvinyl acetate as the gum base. Owing to the elastomeric properties of vinyl acetate-vinyl laurate copolymers, it is possible to dispense with the use of further elastomers in the formulation. Here too, the individual constituents of the formulation are metered successively into a preheated mixer and mixed in the melt.

A disadvantage in the case of use of vinyl acetate-vinyl laurate copolymers is that they are obtained as tough, elastic blocks which cannot be used directly in the customary processes for producing chewing gum mixtures in batch kneaders or extruders. The blocks have to be comminuted beforehand, which is possible only with a high level of cost and inconvenience owing to the tough, elastic material, for example by freezing the material and subsequent comminution. A further means of converting the vinyl acetate-vinyl laurate copolymers to a ready-to-process form is to melt them and to meter them into the kneader or extruder as a melt.

SUMMARY OF THE INVENTION

It was therefore an object of the invention to modify the vinyl acetate-vinyl laurate copolymers in such a way that they are provided in a form which enables metered addition in the course of processing to give chewing gum base without the operator having to carry out the costly and inconvenient process steps mentioned, and with which the polymer resin and/or elastomer content of conventional formulations can be replaced completely or partly. These and other objects are met by utilizing, instead of separate vinyl acetate and vinyl acetate-vinyl laurate copolymers, a solid, homogeneous solid blend of vinyl acetate copolymer and vinyl acetate-vinyl laurate copolymer.

The invention provides homogeneous compounds in solid form comprising
a) from 50 to 90% by weight of polyvinyl acetate and
b) from 10 to 50% by weight of vinyl acetate-vinyl laurate copolymer, based in each case on the total weight of the compound.

DETAILED DESCRIPTION OF THE PREFERRED EMBODIMENTS

The composition is in a homogeneous form, i.e. in the form of particles which comprise both fractions of polyvinyl acetate a) and fractions of vinyl acetate-vinyl laurate copolymer b). The composition present in particulate, room temperature solid form. In general, the particle size is from 1 to 20 mm. Preference is given to granules, pastilles and pellets. In a further preferred embodiment, the particles are powdered with antiblocking agent, for example talc or fumed silica. The antiblocking agent content is preferably up to 5% by weight, based on the weight of the particles.

The compositions contain preferably from 60 to 80% by weight of polyvinyl acetate and from 20 to 40% by weight of vinyl acetate-vinyl laurate copolymer, based in each case on the total weight of the composition, and where the figures in % by weight each add up to 100% by weight. Particular preference is given to compositions comprising from 65 to 75% by weight of polyvinyl acetate and from 25 to 35% by weight of vinyl acetate-vinyl laurate copolymer.

The polyvinyl acetates are generally polyvinyl acetate homopolymers. When the polyvinyl acetate is prepared in the presence of the vinyl acetate-vinyl laurate copolymer, it is possible for small fractions of vinyl laurate to be copolymerized, generally less than 10% by weight, preferably up to 5% by weight, based on the total weight of the copolymer. Preference is given to polyvinyl acetates having a weight-average molecular weight Mw of from 10,000 to 100,000, more preferably from 15,000 to 55,000.

The vinyl acetate-vinyl laurate copolymer contains preferably from 50 to 90% by weight of vinyl acetate units and from 10 to 50% by weight of vinyl laurate units, more preferably from 60 to 80% by weight of vinyl acetate units and from 20 to 40% by weight of vinyl laurate units. The weight-average molecular weight Mw of the vinyl acetate-vinyl laurate copolymer is preferably from 100 000 to 600 000. The weight-average molecular weight Mw was determined in each case by means of size exclusion chromatography, SEC, in THF with a polystyrene standard.

The component a) may also be a mixture of polyvinyl acetates of different molecular weight. Equally, the component b) may be a plurality of vinyl acetate-vinyl laurate copolymers with different copolymer composition and/or different molecular weights.

The compounds can be produced by mixing the melts of one or more polyvinyl acetates a) and one or more vinyl acetate-vinyl laurate copolymers b).

Polyvinyl acetates a) suitable for this purpose and suitable vinyl acetate-vinyl laurate copolymers b) are commercially available, for example Vinnapas® solid resins from Wacker Chemie AG. The polyvinyl acetate component a) and the vinyl acetate-vinyl laurate copolymer component b) can also be prepared in a known manner by means of bulk or solution polymerization. A suitable process is described, for example, in EP 1352914. To this end, the appropriate monomers are polymerized in the presence of initiators, such as peroxide or azo initiators, optionally in a usually alcoholic solvent and optionally in the presence of regulators, at a temperature of generally from 40° C. to 140° C., and any solvent and regulator and residual monomer is distilled off.

To prepare the compounds by means of mixing of the melts of component a) and b), the polyvinyl acetate a) and the vinyl acetate-vinyl laurate copolymer b) can be metered as solids into a preferably preheated stirred tank, kneader or extruder, and are preferably melted and mixed at a temperature of from 80° C. to 140° C. The procedure is preferably such that the polymer with the lower melt viscosity, usually the copolymer b), is initially charged at processing temperature and then the other component, usually the polyvinyl acetate a), is added. The mixing time is generally from 5 to 90 minutes, according to which mixing unit is selected.

The compositions thus obtainable are mechanically comminuted after cooling, for example in a mill or a crusher. The compounds can also be cooled as a melt on a cooling belt in the form of strips, slabs or drops. A further alternative consists in processing the melt to pellets by means of underwater granulation, in which case preference is given to a particle size of from 1 mm to 20 mm for the pellets, and particular preference is given to a particle size of from 3 mm to 10 mm. Solid compositions are thus obtainable in particulate, dosable and free-flowing form.

In a preferred embodiment, the compositions are produced by means of solution polymerization. To this end, the comonomers of component b), vinyl acetate and vinyl laurate, are initially charged in the desired quantitative ratio, and the polymerization is carried out at a temperature of from 40° C. to 120° C. The initiator can be initially charged completely or partly and the remainder can be metered in. The solvent can be initially charged completely or partly and the remainder can be metered in. Suitable solvents are aldehydes, ketones, preferably alkanols such as methanol, ethanol, propanol, and isopropanol. When the monomers of component b) have copolymerized to an extent of from 60 to 100% by weight, preferably from 60 to 90% by weight, vinyl acetate is added to prepare the polyvinyl acetate a). On completion of the metered addition of vinyl acetate and of the metered addition of initiator, it is optionally possible to continue polymerization. Subsequently, the solvent and residual monomer fractions are removed by distillation, and the product is isolated as solid after the melt has been cooled.

In a further preferred embodiment, the compositions are likewise produced by means of solution polymerization, in which case vinyl acetate is polymerized in the presence of the vinyl acetate-vinyl laurate copolymer. To this end, the vinyl acetate-vinyl laurate copolymer is initially charged together with vinyl acetate monomer, and the polymerization is carried out at a temperature of from 40° C. to 120° C. The initiator can be initially charged completely or partly and the remainder can be metered in. The solvent can be initially charged completely or partly and the remainder can be metered in. Suitable solvents are aldehydes, ketones, preferably alkanols such as methanol, ethanol, propanol, and isopropanol. On completion of the metered additions, it is optionally possible to continue polymerization. Subsequently, the solvent and residual monomer fractions are removed by distillation, and the product is isolated as a solid after the melt has been cooled.

The melt obtained in the solution polymerization is worked up and the compounds are obtained as solids analogously to the processes described for the production of the compounds by means of mixing of components a) and b), for example by mechanical comminution after cooling the melt, for example in a mill or a crusher, or application of the melt to a cooling belt and cooling in the form of strips, slabs or drops. A further alternative consists in processing the melt to pellets by means of underwater granulation, in which case a particle size of from 1 mm to 20 mm is preferred and a particle size of from 3 mm to 10 mm is particularly preferred for the pellets. Solid compositions are thus obtainable in particulate, dosable and free-flowing form.

Irrespective of the production, solid clear particles are obtained, in which components a) and b) are distributed homogeneously.

The compositions are suitable especially for the production of chewing gum base. The compositions are preferably used in a proportion of from 10 to 60% by weight based on the total weight of the chewing gum base. In addition to the compositions, these materials generally also comprise elastomer, filler and optionally further additives.

Suitable elastomers for chewing gum base are polyisobutylenes, isobutylene-isoprene copolymers, styrene-butadiene copolymers and natural rubber. The elastomer content is generally from 10 to 50% by weight based on the total weight of the chewing gum base.

The elastomer content is preferably replaced completely or partly by the inventive composition composed of polyvinyl acetate and vinyl acetate-vinyl laurate copolymer.

Suitable fillers are magnesium carbonate, calcium carbonate, magnesium silicates, aluminum silicates, talc, titanium dioxide, calcium phosphate and cellulose ethers. The filler content in the formulation is generally from 10 to 40% by weight, based on the total weight of the chewing gum base.

Further additives are waxes such as paraffin wax or polyethylene wax, plasticizers such as rosins or terpene resins, hardened fats or glyceryl triacetate, emulsifiers such as glyceryl monostearate or lecithin, antioxidants, flavorings and colorings. The use amounts of these additives are known to those skilled in the art.

It should be pointed out that the amounts of the constituents of the chewing gum base stated in % by weight total to 100% by weight in the formulation.

Chewing gum base is produced by the processes customary for this purpose. In general, the constituents of the chewing gum base, if appropriate after a preceding granulation or pulverization step, are mixed, then the mixture is heated to typically from 70° C. to 150° C., generally to give a melt, and then the chewing gum base is extruded or cast into shape.

EXAMPLE 1

A stirred tank is initially charged with 2 kg of isopropanol together with 16 kg of vinyl acetate, 10 kg of vinyl laurate and 7 g of t-butyl peroxo-2-ethylhexanoate, and the polymerization is started by means of heating of the initial charge to 72° C. At the start, 7 g of t-butyl peroxo-2-ethylhexanoate are added and, during the polymerization, 180 g of butyl peroxo-2-ethylhexanoate in 700 g of isopropanol are metered in. 240 minutes after the start, the metered addition of 44 kg of vinyl acetate was commenced and the metered addition was continued over a period of 165 minutes. On completion of metered addition 1, stirring was continued for another 25 minutes, the temperature was increased to 120° C., the tank was evacuated, and solvent and residual monomer were distilled off. The melt was discharged and cooled on a cooling belt to give drop-shaped particles with a size of from 3 to 6 mm. A clear product was obtained with two glass transition temperatures $Tg_1=2°$ C. and $Tg_2=29°$ C., and a molecular weight Mw of 141,000.

EXAMPLE 2

A stirred tank was initially charged with 6 kg of isopropanol and 2 kg of vinyl acetate together with 29 kg of a vinyl acetate-vinyl laurate copolymer (60% by weight of vinyl acetate and 40% by weight of vinyl laurate, Mw=420,000), and the initial charge was heated to 72° C. The polymerization was started by means of addition of 14 g of t-butyl peroxopivalate. After 20 minutes, the metered addition of 100 g of t-butyl peroxo-2-ethylhexanoate in 272 g of isopropanol was started and was continued over a period of 3 hours. 50 minutes after the start of the reaction, the metered addition of 41 kg of vinyl acetate was commenced and was continued over 2.5 hours. On completion of the metered additions, stirring was continued for another 25 minutes, the temperature was increased to 120° C., the tank was evacuated, and solvent and residual monomer were distilled off. The melt was discharged and processed by means of underwater granulation to give granules with a particle size of from 1 to 2 mm. A clear product was obtained with two glass transition temperatures $Tg_1=-1°$ C. and $Tg_2=32°$ C., and a molecular weight Mw of 169,000.

EXAMPLE 3

A laboratory kneader (double-Z kneading hook) was initially charged at from 120° C. to 140° C. with 40 parts by weight of a vinyl acetate/vinyl laurate copolymer (60% by weight of vinyl acetate, to which 40% by weight of vinyl laurate, Mw=420,000), and 60 parts by weight of a vinyl acetate homopolymer (Mw=15,000) were added, and the mixture was kneaded for 1 hour to give a composition. Subsequently, the melt was allowed to solidify to a slab, which was comminuted mechanically to particles with a particle size of from 1 to 20 mm. A clear product was obtained with two glass transition temperatures $Tg_1=0°$ C. and $Tg_2=38°$ C.

EXAMPLE 4

A laboratory kneader (double-Z kneading hook) was initially charged at from 120° C. to 140° C. with 30 parts by weight of a vinyl acetate/vinyl laurate copolymer (60% by weight of vinyl acetate, 40% by weight of vinyl laurate, Mw=420,000), and 70 parts by weight of a vinyl acetate homopolymer (Mw=40,000) were added and the mixture was kneaded for 1 hour to give a composition. Subsequently, the melt was allowed to solidify to a slab, which was comminuted mechanically to particles with a particle size of from 1 to 20 mm. A clear product was obtained with two glass transition temperatures $Tg_1=0°$ C. and $Tg_2=38°$ C.

EXAMPLE 5

Production of a Chewing Gum Base

In a conventional kneader, the following ingredients were processed at 120° C. to give a gum base:
40 parts by weight of the composition of Example 3
20 parts by weight of glyceryl ester of a partially hydrogenated rosin
20 parts by weight of calcium carbonate
10 parts by weight of microcrystalline wax
5 parts by weight of vegetable fat
3.5 parts by weight of glyceryl monostearate
0.5 part by weight of soya lecithin
The mixing time in order to obtain a homogeneous material was 90 minutes.

Example 6

Production of a Chewing Gum Base 35 parts by weight of the composition of Example 2
5 parts by weight of polyvinyl acetate (Mw=15,000)
22 parts by weight of glyceryl ester of a partially hydrogenated rosin
25 parts by weight of talc
4 parts by weight of paraffin wax
5 parts by weight of hydrogenated rapeseed oil
4 parts by weight of glyceryl monostearate
The mixing time in order to obtain a homogeneous material was 90 minutes.

COMPARATIVE EXAMPLE 7

Production of the Chewing Gum Base in Conventional Formulation 4 parts by weight of butyl rubber
7 parts by weight of polyisobutylene
26 parts by weight of polyvinyl acetate (Mw=15,000)
21 parts by weight of glyceryl ester of a partially hydrogenated rosin
24 parts by weight of talc
8 parts by weight of microcrystalline wax
6 parts by weight of hydrogenated rapeseed oil
4 parts by weight of glyceryl monostearate
The mixing time in order to obtain a homogeneous material was 150 minutes.

The comparison of Examples 5 and 6 with comparative Example 7 is that exchange of the elastomer component and of the polymer resin component for the inventive composition significantly reduces the production time of a chewing gum base. Furthermore, the inventive compositions are significantly easier to process compared to conventional vinyl acetate-vinyl laurate elastomers, since they are present in ready-to-use, particulate form.

EXAMPLE 8

Production of a Sugar-Free Chewing Gum

In a laboratory kneader, a chewing gum mixture was produced at from 45° C. to 60° C. with the following ingredients:
25 parts by weight of chewing gum base from Example 5

15 parts by weight of xylitol
52 parts by weight of sorbitol
6.8 parts by weight of sorbitol syrup
1 part by weight of peppermint oil
0.2 part by weight of aspartame

What is claimed is:

1. In a process for the preparation of a chewing gum comprising a chewing gum base composition containing a vinyl acetate-vinyl laurate copolymer and further additives, the improvement comprising incorporating the vinyl acetate-vinyl laurate copolymer in the form of a homogenous solid mixture comprising:
   a) from 50 to 90 percent by weight of a polyvinyl acetate polymer, and
   b) from 10 to 50 percent by weight of a vinyl acetate-vinyl laurate copolymer, into the chewing gum base composition wherein the percents by weight are based on the total weight of the homogenous solid mixture.

2. The process of claim 1, wherein the chewing gum base composition comprises from 10 to 60 weight percent of the homogenous solid mixture, based on the weight of the chewing gum base composition.

3. The process of claim 1, wherein the chewing gum base composition consists of the homogenous solid mixture and further additives.

4. The process of claim 1, wherein the vinyl acetate-vinyl laurate copolymer contains 60-80 weight percent of vinyl acetate-derived moieties and 20-40 weight percent of vinyl laurate-derived moieties based on the weight of the vinyl acetate-vinyl laurate copolymer.

5. The process of claim 1, wherein the homogenous solid mixture is prepared by a process comprising solution polymerizing comonomers including vinyl acetate and vinyl laurate to form a vinyl acetate-vinyl laurate copolymer b), following which vinyl acetate monomer is added and polymerized after a monomer conversion of from 60 to 100% by weight of the comonomers used to form copolymer b), and isolating the product as a solid, wherein the homogenous solid mixture comprises from 50-90% by weight, based on the total weight of the homogenous solid mixture, of a) a polyvinyl acetate polymer containing more than 90% by weight of vinyl acetate derived moieties based on the weight of the polyvinyl acetate polymer, and from 10 to 50% by weight based on the total weight of the homogenous solid mixture, of b) a vinyl acetate-vinyl laurate copolymer containing 10-50% of vinyl laurate derived moieties based on the weight of the polyvinyl acetate-vinyl laurate copolymer.

6. The process of claim 1, wherein the polyvinyl acetate polymer contains less than 10 weight percent of vinyl laurate-derived moieties, based on the weight of the polyvinyl acetate polymer.

7. The process of claim 1, wherein the polyvinyl acetate polymer contains less than 5 weight percent of vinyl laurate-derived moieties, based on the weight of the polyvinyl acetate polymer.

8. The process of claim 1, wherein the homogenous solid mixture is prepared by separately preparing a polyvinyl acetate polymer and a vinylacetate-vinyl laurate copolymer, and blending the polyvinyl acetate polymer and the vinyl acetate-vinyl laurate copolymer in the melt, and solidifying the melt.

9. The process of claim 1, wherein the homogenous solid mixture is prepared by dissolving a vinyl acetate-vinyl laurate copolymer in solvent, adding vinyl acetate monomer, polymerizing the vinyl acetate monomer, and removing solvent to form a homogenous solid mixture.

10. The process of claim 1, wherein the homogenous solid mixture comprises from 65 to 75 weight percent polyvinyl acetate polymer and 35 to 25 weight percent vinyl acetate-vinyl laurate copolymer, based on the weight of the homogenous solid mixture.

11. The process of claim 1, wherein the weight-average molecular weight Mw of the polyvinyl acetate polymer a) is from 10,000 to 100,000 and the weight-average molecular weight Mw of the vinyl acetate-vinyl laurate copolymer b) is from 100,000 to 600,000.

* * * * *